United States Patent [19]

Takematsu et al.

[11] Patent Number: 4,929,273
[45] Date of Patent: May 29, 1990

[54] N-BENZYL-2-(4-FLUORO-3-TRIFLUOROME-THYLPHENOXY)BUTANOIC AMIDE AND HERBICIDAL COMPOSITION CONTAINING THE SAME

[75] Inventors: Tetsuo Takematsu; Yasutomo Yakeuchi, both of Utsunomiya; Mitsuaki Takenaka, Ube; Seiji Takamura, Ube; Akio Matsushita, Ube, all of Japan

[73] Assignee: Ube Industries, Ltd., Ube, Japan

[21] Appl. No.: 412,635

[22] Filed: Sep. 22, 1989

Related U.S. Application Data

[63] Continuation of Ser. No. 29,432, Mar. 23, 1987.

[30] Foreign Application Priority Data

Mar. 28, 1986 [JP] Japan .................. 61-68805

[51] Int. Cl.$^5$ .................. A01N 37/18; C07C 103/178
[52] U.S. Cl. .................. 71/118; 71/90; 71/93; 71/100; 71/120; 564/175
[58] Field of Search .................. 564/175; 71/118

[56] References Cited

U.S. PATENT DOCUMENTS 4,332,961  6/1982  Takahashi et al. .................. 71/108
4,753,674  6/1988  Takematsu et al. .................. 71/118

FOREIGN PATENT DOCUMENTS 0029645  2/1984  Japan .................. 564/175

OTHER PUBLICATIONS

T. Fujita, "Chemical Regulation of Plant", vol. 5, No. 2, pp. 124–141.

Primary Examiner—Glennon H. Hollrah
Assistant Examiner—Susan P. Treanor
Attorney, Agent, or Firm—Frishauf, Holtz, Goodman & Woodward

[57] ABSTRACT

There are disclosed N-benzyl-2-(4-fluoro-3-trifluoromethylphenoxy)butanoic amide represented by the formula:

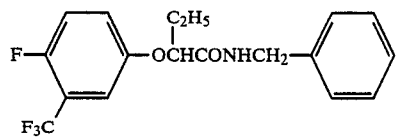

and a herbidical composition containing the same as an active ingredient.

6 Claims, No Drawings

N-BENZYL-2-(4-FLUORO-3-TRIFLUOROME-THYLPHENOXY)BUTANOIC AMIDE AND HERBICIDAL COMPOSITION CONTAINING THE SAME

This application is a continuation of application Ser. No. 029,432, filed Mar. 23, 1987.

BACKGROUND OF THE INVENTION

This invention relates to an N-benzyl-2-(4-fluoro3-trifluoromethylphenoxy)butanoic amide which is a novel compound and a herbicidal composition containing the same.

Heretofore, as compounds which show herbicidal effects, there have been known various compounds. For example, as function of killing weeds of a 2-phenoxybutanoic amide type compounds, there have been disclosed in U.S. Pat. Nos. 3,840,596, No. 3,852,345, No. 4,051,184, No. 4,087,277, No. 4,116,677 and No. 4,119,433; Japanese Provisional Patent Publications No. 67653/1983, No. 113155/1983 and No. 29645/1984; and the like.

The above six U.S. Patents each discloses amide derivatives of aliphatic amines such as lower alkylamines, lower alkynylamines, cyanoalkylamines and lower alkoxyamines with 2-phenoxybutanoic acid, and there is neither disclosed in the specification of the above prior art references concerning amide derivatives of benzylamine to be used in the present invention and 2-phenoxybutanoic acid, i.e., N-benzyl-2-phenoxybutanoic amide series compounds at all.

Further, in the above Japanese Provisional patent Publications No. 67653/1983, No. 113155/1983 and No. 29645/1984, there are disclosed summarily that the phenoxyalkanoic amide derivative represented by the following general formula:

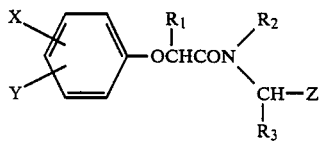

wherein X and Y each represent a hydrogen atom, a lower alkyl group, a lower alkoxy group, a propionyl group, a nitro group, a cyano group or a halogen atom; $R_1$ represents a lower alkyl group; $R_2$ represents a hydrogen atom, a lower alkyl group or a lower alkenyl group; $R_3$ represents a hydrogen atom or a lower alkyl group; and Z represents a phenyl group, a furyl group, a thienyl group, a pyridyl group or a naphthyl group and hydrogen atoms of the phenyl group may be substituted by a lower alkyl group, a lower alkoxy group, a chlorine atom or a nitro group,
has a herbicidal function. However, the compound of the present invention is that X in the above general formula is a fluorine atom and Y is a trifluoromethyl group and there is not disclosed concerning the compound in the above three Japanese Provisional Patent Publications at all.

Further, in the above Japanese Provisional Patent Publication No. 29645/1984, there is disclosed that 2-phenoxyalkanoic amide derivatives represented by the following general formula:

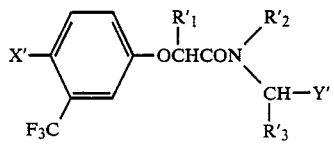

wherein X' represents a hydrogen atom or a halogen atom; $R'_1$ represents a lower alkyl group; $R'_2$ represents a hydrogen atom, a lower alkyl group, a lower alkenyl group, a lower alkynyl group or a lower alkoxy group; $R'_3$ represents a hydrogen atom or a lower alkyl group; and Y' represents a phenyl group, a thienyl group, a pyridyl group or a furyl group and hydrogen atoms of the phenyl group may be replaced by a lower alkyl group, a lower alkoxy group or a halogen atom,
has a herbicidal function. However, in the above publication, while the substituent X' in the compound represented by the above formula is defined as a halogen atom, only the case where the halogen atom is a chlorine atom is disclosed in the examples thereof and the herbicidal effect of the case is insufficient.

SUMMARY OF THE INVENTION

An object of the present invention is to provide a novel compound and a herbicidal composition containing the same in which broadleaf weeds which is difficult to control and causes serious problem for growing a principal grain, particularly barley, wheat, etc. are effectively prevented to grow and removed.

An N-benzyl-2-(4-fluoro-3-trifluoromethylphenoxy)-butanoic amide of the present invention comprises having the formula (I) shown below:

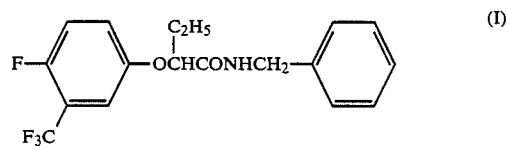

and a herbicidal composition of the present invention comprises containing the N-benzyl-2-(4-fluoro-3-trifluoromethylphenoxy)butanoic amide as an effective ingredient.

PREFERRED EMBODIMENTS OF THE INVENTION

The N-benzyl-2-(4-fluoro-3-trifluoromethylphenoxy) butanoic amide of the present invention has extremely low in toxicity to a homoiothermic animal and $LD_{50}$ thereof is 5000 mg/Kg or more in both cases of an oral administration and a subcutaneous administration to rats. Further, no stimulation to eyes or skin is observed and no toxicity to fishes and shellfishes as well as no offensive odor are present so that it has various excellent characteristic features. Also, the compound represented by the formula (I) may be an optically active isomer and (-)-N-benzyl-2-(4-fluoro-3-trifluoromethylphenoxy)butanoic amide is particularly preferred in view of strong herbicidal activity when prepared a herbicidal composition.

The N-benzyl-2-(4-fluoro-3-trifluoromethylphenoxy)butanoic amide represented by the formula (I) of the present invention can be prepared, for example, by the following reaction formula (1) or (2):

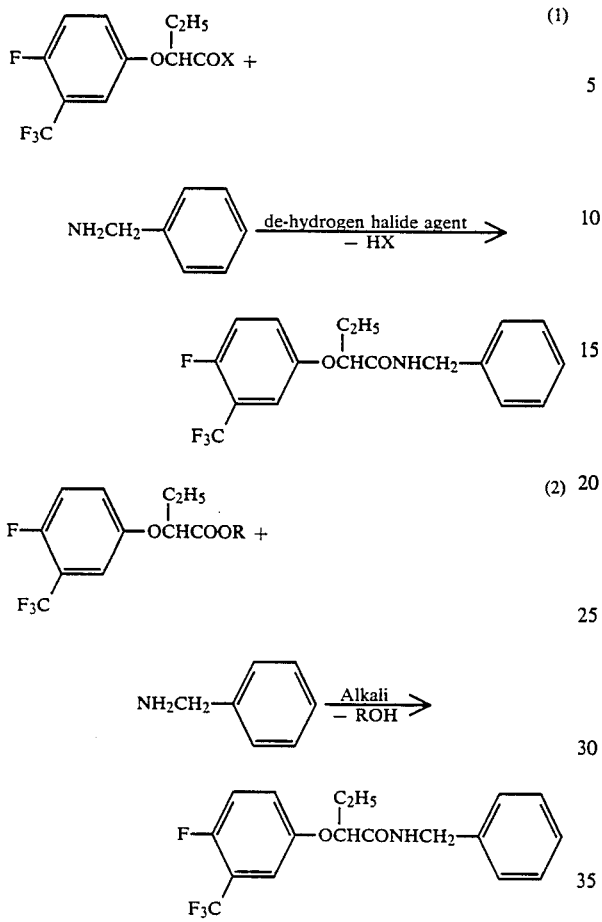

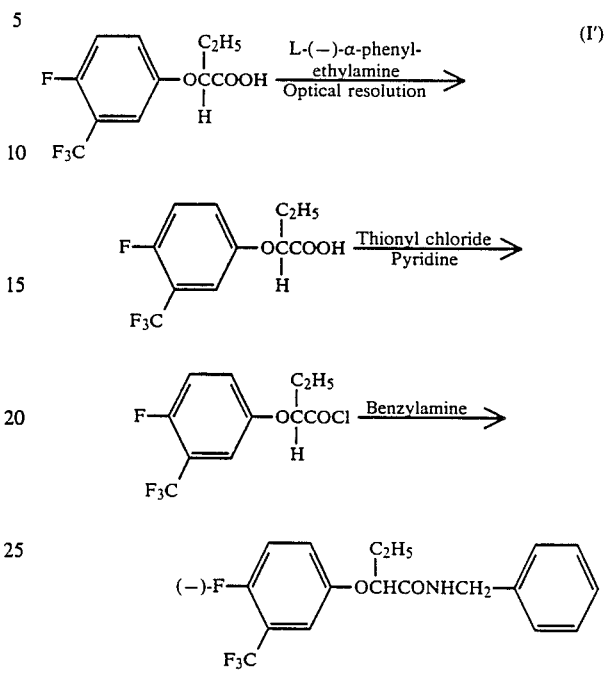

wherein, in the above formulae, X represents a halogen atom, and R represents a lower alkyl group.

The reaction in the formula (1) may preferably be carried out in the presence of a suitable solvent by adding, as the de-hydrogen halide agent, a tertiary amine such as triethylamine, dimethylaniline and pyridine, or a carbonate such as sodium carbonate and potassium carbonate. As the solvent to be used in the reaction, there may be mentioned an aromatic hydrocarbon such as benzene, toluene and xylene; an ether such as diethylether, tetrahydrofuran and dioxane; and a ketone such as dimethyl ketone and methyl ethyl ketone. The reaction temperature varies depending upon the kinds of reagents and solvents to be used and is not particularly limited, but it is preferably be carried out at −10 to 100 °C. The reaction time may be about 1 to 10 hours. Also, the reaction of the formula (2) may preferably be carried out by adding a metal lower alcoholate such as sodium methoxide and sodium ethoxide in an amount of 0.03 to 0.3 mole per mole of a reaction substrate. As the reaction solvent, there may be used a lower alcohol such as methanol, ethanol and propanol, and an aromatic hydrocarbon such as benzene, toluene and xylene. The reaction temperature and time varies depending upon a kind and amount of the alkali to be added and the solvent to be added and are not particularly limited, but, for example, it can be carried out at a temperature of 0 to 50 °C. for 1 to 15 hours whereby the compound can be obtained with good yield.

Further, the optically active isomer of the compound represented by the formula (I) can be prepared, for example by the following reaction formula (3):

While the herbicidal composition of the present invention contains N-benzyl-2-(4-fluoro-3-trifluoromethylphenoxy)butanoic amide represented by the formula (I) as an active ingredient, other compounds which have herbicidal effect, than the compound represented by the formula (I) may be contained as active ingredients.

As the compounds having herbicidal effects, there may be mentioned, for example, the compound represented by the following formula (compound A):

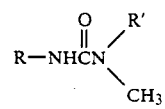

wherein R represents

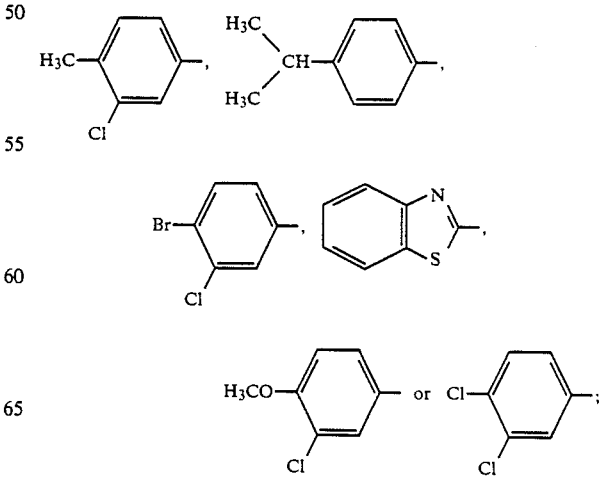

and R' represents —OCH₃ or —CH₃, more specifically, N-3-chloro-4-methylphenyl-N',N'-dimethylurea (compound A-1), N-4-isopropylphenyl-N',N'-dimethylurea (compound A-2) and N-3,4-dichlorophenyl-N'-methyl-N'-methoxyurea (compound A-3), etc.; 4-amino-6-(1,1-dimethylethyl)-3-(methylthio)-1,2,4-triazin-5(4H)-one (compound B); α,α,α-trifluoro-2,6-dinitro-N,N-dipropyl-p-toluidine (compound C); S-(p-chlorobenzyl)-N,N-diethylthiolcarbamate (compound D); and the like, and at least one of the above compounds may be contained in the herbicidal composition of the present invention as active ingredients with the compound represented by the formula (I).

The herbicidal composition containing the N-benzyl-2-(4-fluoro-3-trifluoromethylphenoxy)butanoic amide as an active ingredient may be formulated for use to the preparations of any form commonly employed as the agricultural formulation, by using an inert solid carrier, liquid carrier, emulsifying dispersant and the like, for example, granules, dusts, emulsions, wettable powders, tablets, lubricants, aerosols, fumigants and so on. As the inert carriers, there may be mentioned, for example, talc, clay, kaoline, diatomaceous earth, calcium carbonate, potassium chlorate, saltpeter, wood powder, nitrocellulose, starch, benzene, xylene, n-hexane, gum arabic, vinyl chloride, carbon dioxide, feon, propane, butane and the like. Further, it may be optionally blended with any auxiliary agents for preparation, for example, spreaders, diluents, surface active agents, solvents and the like. Moreover, it may be optionally admixed with fungicides, insecticides and other herbicides; urea, ammonium sulfate, ammonium phosphate, potassium salts and other fertilizers; soil conditioners and the like.

An amount of the N-benzyl-2-(4-fluoro-3-trifluoromethylphenoxy)butanoic amide to be contained in the herbicidal composition of the present invention is within the range of about 1 to about 90 % by weight.

When the herbicidal composition containing the compound represented by the formula (I) of the present invention as an active ingredient is applied to weeds, it acts to reduce chlorophyll in the weeds whereby inhibit photosynthesis thereof and kills away or controls the weeds.

In the following, the present invention will be explained in more detail by referring to Examples and Experiments. All parts in each Examples are given by parts by weight hereinafter unless otherwise stated.

EXAMPLES

EXAMPLE 1

In accordance with the above reaction formula (1), the compound of the present invention was prepared. First, after 4.2 g (0.039 mole) of benzylamine and 3.1 g (0.039 mole) of pyridine were dissolved in 50 ml of toluene, 11.0 g (0.039 mole) of 2-(4-fluoro-3-trifluoromethylphenoxy)butanoic chloride was gradually added dropwise to the solution under stirring at room temperature. After dropwise addition, the mixture was further stirred for 3 hours at room temperature, and the reaction mixture was then washed with a diluted hydrochloric acid, diluted sodium hydroxide and water with the order. After the toluene layer was dehydrated with anhydrous sodium sulfate, toluene was distilled out under reduced pressure. Resulting crude crystal was recrystallized from toluene to give 12.8 g (Yield: 92 %) of N-benzyl-2-(4-fluoro-3-trifluoromethylphenoxy)-butanoic amide having a melting point of 75 to 76 ° C. as colorless needle crystals. Elemental analysis

|  | C | H | N |
|---|---|---|---|
| Theoretical | 60.84 | 4.82 | 3.94 |
| Measured | 60.99 | 5.06 | 4.01 |

EXAMPLE 2

In accordance with the above reaction formula (2), the compound of the present invention was prepared. First, after 147 g (0.50 mole) of 2-(4-fluoro-3-trifluoromethylphenoxy)butanic acid ethyl ester and 53.5 g (0.50 mole) of benzylamine were dissolved in 314 ml of toluene, 20.0 g (0.10 mole) of sodium methoxide (28 % methanol solution) was added to the solution and the mixture was stirred at room temperature for 7 hours.

Then, after the reaction mixture was washed with a 1N aqueous hydrochloric acid and water with the order, and dehydrated with anhydrous magnesium sulfate, toluene was distilled out under reduced pressure. To the resulting yellowish oily product was added 200 ml of n-hexane, and the mixture was stirred to give crude crystal. Resulting crude crystal was recrystallized from ethanol to give 153 g (Yield: 86 %) of N-benzyl-2-(4-fluoro-3-trifluoromethylphenoxy)butanoic amide having a melting point of 75 to 76 ° C. as colorless needle crystals.

EXAMPLE 3

In accordance with the above reaction formula (2), the compound of the present invention was prepared. First, after 140 g (0.50 mole) of 2-(4-fluoro-3-trifluoromethylphenoxy)butanic acid methyl ester and 53.5 g (0.50 mole) of benzylamine were dissolved in 300 ml of methanol, 10.0 g (0.052 mole) of sodium methoxide (28 % methanol solution) was added to the solution and the mixture was stirred at room temperature for 10 hours.

Then, methanol was distilled out under reduced pressure, and the product was dissolved with addition of 360 ml of toluene. Thereafter, the reaction mixture was washed with a 1N aqueous hydrochloric acid and water with the order, and dehydrated with anhydrous magnesium sulfate, toluene was distilled out under reduced pressure. To the resulting yellowish oily product was added 200 ml of n-hexane, and the mixture was stirred to give crude crystal. Resulting crude crystal was recrystallized from ethanol to give 148 g (Yield: 83 %) of N-benzyl-2-(4-fluoro-3-trifluoromethylphenoxy)-butanoic amide having a melting point of 75 to 76 ° C. as colorless needle crystals.

EXAMPLE 4

10 parts of N-benzyl-2-(4-fluoro-3-trifluoromethylphenoxy)butanoic amide, 80 parts of xylene and 10 parts of Solvol 800 (surface active agent, trade name) were mixed and dissolved to give an emulsion type herbicidal composition.

EXAMPLE 5

50 parts of N-benzyl-2-(4-fluoro-3-trifluoromethylphenoxy)butanoic amide, 30 parts of kaolin, 15 parts of bentonite and 5 parts of sodium lignosulfonate were blended and kneaded to give a wettable powder type herbicidal composition.

Experiment 1

Soil treatment tests for cereal weeds

A pot having an area of 1/5000 are was packed with an upland soil (sandy loam soil) and then seeds of the following plants were sowed therein.

| | |
|---|---|
| Wheat | *Triticum aestivum* |
| Barley | *Hordeum vulgare* |
| Oats | *Avena sativa* |
| Cleavers | *Galium aparine* |
| Speedwell | *Veronica persica* |
| White dead nettle | *Lamium purpureum* |
| Red poppy | *Papaver rhoeas* |
| Matoricaria | *Matoricaria inodora* |

Then, after covering seeds with soil, diluted solution of a wettable powder prepared according to Example 5 of the present compound and diluted solutions of wettable powders in which each compound shown in Tables 1 and 2 prepared in the same manner as in Example 5 were uniformly sprayed on the surface layer thereof with a dosage shown in the tables by using a pressure sprayer. Three weeks after the spreading treatment, the herbicidal effects of each test compound were assessed. The results are shown in Tables 1 and 2. In Table 1, compounds No. 1 to No. 4 are compounds disclosed in Japanese Provisional Patent Publication No. 67653/1983, compounds No. 5 and 6 are those disclosed in Japanese Provisional Patent publication No. 113155/1983, compounds No. 7 to No. 9 are compounds disclosed in Japanese Provisional Patent Publication No. 113156/1983 and compounds No. 10 to 12 are those disclosed in Japanese Provisional Patent Publication No. 29645/1984. In Table 2, compounds No. 20 to No. 21 are compounds disclosed in U.S. Pat. No. 4,051,184 and compound No. 22 is a compound disclosed in U.S. Pat. No. 4,087,277. Further, in Tables 1 and 2, the crop injury and herbicidal effects are evaluated according to the following standards:

5: All killed, 4: Severely damaged,
3: Moderately damaged, 2: Slightly damaged,
1: Minor damaged, and 0: None (normal development).

TABLE 1

| Compound No. | Compound to be tested | Dosage [g/a] | Crop injury |||  Herbicidal effect |||||
|---|---|---|---|---|---|---|---|---|---|---|
| | | | *Triticum aestivum* | *Hordeum vulgare* | *Avena sativa* | *Galium aparine* | *Veronica persica* | *Lamium purpureum* | *Papaver rhoeas* | *Matoricaria inodora* |
| | Compound of the present invention m.p. 75 to 76° C. | 5.0 | 0 | 0 | 0 | 5 | 5 | 5 | 5 | 5 |
| | | 2.5 | 0 | 0 | 0 | 5 | 5 | 5 | 5 | 5 |
| | | 1.25 | 0 | 0 | 0 | 4 | 5 | 5 | 4 | 5 |
| 1 | Cl—⟨benzene⟩—OCH(C$_2$H$_5$)CONHCH$_2$—⟨benzene⟩ ; CH$_3$ substituent; m.p. 95~97° C. | 5.0 | 0 | 0 | 0 | 0 | 0 | 1 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| 2 | Cl—⟨benzene⟩—OCH(C$_2$H$_5$)CON(CH$_3$)(CH$_2$—⟨benzene⟩); CH$_3$ substituent; $n_D^{25.6}$ 1.5579 | 5.0 | 0 | 0 | 0 | 0 | 1 | 0 | 2 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |
| 3 | CH$_3$, Cl—⟨benzene⟩—OCH(C$_2$H$_5$)CONHCH$_2$—⟨benzene⟩; CH$_3$; m.p. 111~113° C. | 5.0 | 0 | 0 | 0 | 1 | 3 | 1 | 2 | 1 |
| | | 2.5 | 0 | 0 | 0 | 1 | 2 | 0 | 1 | 0 |
| | | 1.25 | 0 | 0 | 0 | 0 | 0 | 0 | 0 | 0 |
| 4 | CH$_3$, Cl—⟨benzene⟩—OCH(C$_2$H$_5$)CON(CH$_3$)(CH$_2$—⟨benzene⟩); CH$_3$; $n_D^{25.2}$ 1.5561 | 5.0 | 0 | 0 | 0 | 0 | 1 | 0 | 0 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |

TABLE 1-continued

| Compound No. | Compound to be tested | Dosage [g/a] | Crop injury | | | Herbicidal effect | | | | |
|---|---|---|---|---|---|---|---|---|---|---|
| | | | Triticum aestivum | Hordeum vulgare | Avena sativa | Galium aparine | Veronica persica | Lamium purpureum | Papaver rhoeas | Matoricaria inodora |
| 5 | 4-Cl-3,5-(CH$_3$)$_2$-C$_6$H$_2$-OCH(C$_2$H$_5$)CONHCH$_2$-(3-pyridyl) m.p. 88~92° C. | 5.0<br>2.5<br>1.25 | 0<br>0<br>0 | 0<br>0<br>0 | 0<br>0<br>0 | 1<br>0<br>0 | 2<br>2<br>0 | 2<br>1<br>0 | 3<br>1<br>0 | 1<br>1<br>0 |
| 6 | 3,4-Cl$_2$-C$_6$H$_3$-OCH(C$_2$H$_5$)CONHCH$_2$-(3-pyridyl) n$_D^{26}$ 1.5736 | 5.0<br>2.5<br>1.25 | 0<br>0<br>0 | 0<br>0<br>0 | 0<br>0<br>0 | 0<br>0<br>0 | 2<br>0<br>0 | 1<br>0<br>0 | 2<br>1<br>0 | 2<br>0<br>0 |
| 7 | 4-CH$_3$O-C$_6$H$_4$-OCH(C$_2$H$_5$)CONHCH$_2$-C$_6$H$_5$ m.p. 72~74° C. | 5.0<br>2.5<br>1.25 | 0<br>0<br>0 | 0<br>0<br>0 | 0<br>0<br>0 | 0<br>0<br>0 | 0<br>0<br>0 | 0<br>0<br>0 | 0<br>0<br>0 | 0<br>0<br>0 |
| 8 | 4-CH$_3$-3-NO$_2$-C$_6$H$_3$-OCH(C$_2$H$_5$)CONHCH$_2$-C$_6$H$_5$ m.p. 99~100° C. | 5.0<br>2.5<br>1.25 | 0<br>0<br>0 | 0<br>0<br>0 | 0<br>0<br>0 | 1<br>0<br>0 | 2<br>1<br>0 | 1<br>0<br>0 | 1<br>1<br>0 | 2<br>1<br>0 |
| 9 | 3-NC-C$_6$H$_4$-OCH(C$_2$H$_5$)CONHCH$_2$-C$_6$H$_5$ m.p. 82~85° C. | 5.0<br>2.5<br>1.25 | 0<br>0<br>0 | 0<br>0<br>0 | 0<br>0<br>0 | 0<br>0<br>0 | 2<br>0<br>0 | 1<br>0<br>0 | 1<br>0<br>0 | 2<br>0<br>0 |
| 10 | 3-CF$_3$-C$_6$H$_4$-OCH(C$_2$H$_5$)CONHCH$_2$-C$_6$H$_5$ n$_D^{23}$ 1.5146 | 5.0<br>2.5<br>1.25 | 0<br>0<br>0 | 0<br>0<br>0 | 0<br>0<br>0 | 1<br>0<br>0 | 3<br>0<br>0 | 2<br>0<br>0 | 2<br>1<br>0 | 1<br>0<br>0 |
| 11 | 3-CF$_3$-C$_6$H$_4$-OCH(C$_2$H$_5$)CONHCH$_2$-(2-Cl-C$_6$H$_4$) m.p. 66~68° C. | 5.0<br>2.5<br>1.25 | 0<br>0<br>0 | 0<br>0<br>0 | 0<br>0<br>0 | 3<br>1<br>0 | 3<br>1<br>1 | 2<br>1<br>1 | 2<br>2<br>0 | 2<br>1<br>0 |
| 12 | 4-Cl-3-CF$_3$-C$_6$H$_3$-OCH(C$_2$H$_5$)CONHCH$_2$-C$_6$H$_5$ m.p. 93~95° C. | 5.0<br>2.5<br>1.25 | 0<br>0<br>0 | 0<br>0<br>0 | 0<br>0<br>0 | 4<br>2<br>0 | 4<br>3<br>1 | 4<br>1<br>0 | 2<br>2<br>1 | 3<br>1<br>0 |

TABLE 1-continued

| Compound No. | Compound to be tested | Dosage [g/a] | Crop injury | | | Herbicidal effect | | | | |
|---|---|---|---|---|---|---|---|---|---|---|
| | | | Triticum aestivum | Hordeum vulgare | Avena sativa | Galium aparine | Veronica persica | Lamium purpureum | Papaver rhoeas | Matoricaria inodora |
| 13 | F—[benzene]—OCH₂CONHCH₂—[phenyl], CF₃ substituent, m.p. 70~73° C. | 5.0<br>2.5<br>1.25 | 0<br>0<br>0 | 0<br>0<br>0 | 0<br>0<br>0 | 0<br>0<br>0 | 0<br>0<br>0 | 0<br>0<br>0 | 0<br>0<br>0 | 0<br>0<br>0 |
| 14 | F—[benzene]—OCH(CH₃)CONHCH₂—[phenyl], CF₃ substituent, m.p. 64~66° C. | 5.0<br>2.5<br>1.25 | 0<br>0<br>0 | 0<br>0<br>0 | 0<br>0<br>0 | 0<br>0<br>0 | 0<br>0<br>0 | 0<br>0<br>0 | 0<br>0<br>0 | 0<br>0<br>0 |
| 15 | F—[benzene]—OCH(C₃H₇)CONHCH₂—[phenyl], CF₃ substituent, m.p. 84~86° C. | 5.0<br>2.5<br>1.25 | 0<br>0<br>0 | 0<br>0<br>0 | 0<br>0<br>0 | 0<br>0<br>0 | 2<br>0<br>0 | 1<br>0<br>0 | 2<br>1<br>0 | 3<br>1<br>0 |
| 16 | F—[benzene]—OCH(C₂H₅)CONHCH₂—[phenyl with CH₃], CF₃ substituent, m.p. 94~96° C. | 5.0<br>2.5<br>1.25 | 0<br>0<br>0 | 0<br>0<br>0 | 0<br>0<br>0 | 3<br>1<br>0 | 3<br>3<br>1 | 3<br>2<br>0 | 2<br>2<br>0 | 2<br>1<br>0 |
| 17 | F—[benzene]—OCH(C₂H₅)CONHCH₂—[phenyl with Cl], CF₃ substituent, m.p. 82~83° C. | 5.0<br>2.5<br>1.25 | 0<br>0<br>0 | 0<br>0<br>0 | 0<br>0<br>0 | 2<br>0<br>0 | 3<br>3<br>0 | 3<br>2<br>0 | 2<br>1<br>0 | 2<br>1<br>0 |
| 18 | F—[benzene]—OCH(C₂H₅)CONHCH₂—[furyl, O], CF₃ substituent, m.p. 73~74° C. | 5.0<br>2.5<br>1.25 | 0<br>0<br>0 | 0<br>0<br>0 | 0<br>0<br>0 | 0<br>0<br>0 | 0<br>0<br>0 | 0<br>0<br>0 | 0<br>0<br>0 | 0<br>0<br>0 |
| 19 | F—[benzene]—OCH(C₂H₅)CONHCH₂—[thienyl, S], CF₃ substituent, m.p. 73~75° C. | 5.0<br>2.5<br>1.25 | 0<br>0<br>0 | 0<br>0<br>0 | 0<br>0<br>0 | 3<br>1<br>0 | 3<br>3<br>0 | 3<br>2<br>0 | 2<br>1<br>0 | 2<br>1<br>0 |

TABLE 2

| Compound No. | Compound to be tested | Dosage [g/a] | Damage* | Herbicidal effect | | |
|---|---|---|---|---|---|---|
| | | | Triticum aestivum | Galium aparine | Veronica persica | Papaver rhoeas |
| | Compound of the present invention | 5.0<br>2.5 | 0<br>0 | 5<br>5 | 5<br>5 | 5<br>5 |

TABLE 2-continued

| Compound No. | Compound to be tested | Dosage [g/a] | Damage* Triticum aestivum | Herbicidal effect Galium aparine | Veronica persica | Papaver rhoeas |
|---|---|---|---|---|---|---|
| | m.p. 75 to 76° C. | 1.25 | 0 | 4 | 5 | 4 |
| 20 | 2,4-Cl$_2$-C$_6$H$_3$-OCH(C$_2$H$_5$)CONH-C(CH$_3$)$_2$-C≡CH<br>m.p. 97–98° C. | 5.0<br>2.5<br>1.25 | 2<br>0<br>0 | 3<br>1<br>0 | 3<br>2<br>0 | 1<br>1<br>0 |
| 21 | 3,5-(CH$_3$)$_2$-C$_6$H$_3$-OCH(C$_2$H$_5$)CONH-C(CH$_3$)$_2$-C≡CH<br>m.p. 86–88° C. | 5.0<br>2.5<br>1.25 | 2<br>0<br>0 | 2<br>0<br>0 | 3<br>1<br>0 | 1<br>0<br>0 |
| 22 | 2,4-Cl$_2$-C$_6$H$_3$-OCH(C$_2$H$_5$)CONH-C(CH$_3$)$_2$-C≡N<br>m.p. 153–154° C. | 5.0<br>2.5<br>1.25 | 0<br>0<br>0 | 1<br>0<br>0 | 4<br>2<br>0 | 1<br>0<br>0 |
| 23 | 4-F-3-CF$_3$-C$_6$H$_3$-OCH(C$_2$H$_5$)CONH-C(CH$_3$)$_2$-C≡CH<br>m.p. 77–79° C. | 5.0<br>2.5<br>1.25 | 0<br>0<br>0 | 0<br>0<br>0 | 1<br>0<br>0 | 1<br>0<br>0 |
| 24 | 4-F-3-CF$_3$-C$_6$H$_3$-OCH(C$_2$H$_5$)CONH-CH(CH$_3$)-C≡CH<br>m.p. 68–69° C. | 5.0<br>2.5<br>1.25 | 0<br>0<br>0 | 0<br>0<br>0 | 1<br>0<br>0 | 0<br>0<br>0 |
| 25 | 4-F-3-CF$_3$-C$_6$H$_3$-OCH(C$_2$H$_5$)CONHCH$_2$C≡CH<br>m.p. 53–54° C. | 5.0<br>2.5<br>1.25 | 0<br>0<br>0 | 0<br>0<br>0 | 1<br>0<br>0 | 1<br>1<br>0 |

*Damage: Crop damage from herbicide

EXPERIMENT 2

Foliar treatment tests for cereal weeds

A pot having an area of 1/5000 are was packed with an upland soil (sandy loam soil) and then seeds of the following plants were sowed therein.

| | |
|---|---|
| Wheat | Triticum aestivum |
| Barley | Hordeum vulgarae |
| Oats | Avena sativa |
| Cleavers | Galium aparine |
| Speedwell | Veronica persica |
| White dead nettle | Lamium purpureum |
| Red poppy | Papaver rhoeas |
| Matoricaria | Matoricaria inodora |

When wheat, barley and orats grew up to 2 to 3 leaf stage, cleavers grew up to 4 to 5 leaf stage and other weeds grew up to 2 leaf stage, each wettable powder of sample compounds, which had been prepared in the same manner as in Experiment 1 above, was sprayed uniformly with a dosage shown in Tables 3 and 4 by using a pressure sprayer. Three weeks after the spreading treatment, the herbicidal effects of each test compound were assested. The results are shown in Tables 3 and 4. Standard of assessment of the crop injury and the herbicidal effects in the Tables are the same with Experiment 1.

TABLE 4

| Compound to be tested | Dosage [g/a] | Damage* Triticum aestivum | Herbicidal effects | | |
|---|---|---|---|---|---|
| | | | Galium aparine | Veronica persica | Papaver rhoeas |
| Compound of the present invention | 5.0 | 0 | 5 | 5 | 5 |
| | 2.5 | 0 | 5 | 5 | 5 |
| | 1.25 | 0 | 5 | 5 | 5 |
| Compound No. 20 | 5.0 | 0 | 2 | 2 | 3 |
| | 2.5 | 0 | 1 | 1 | 0 |
| | 1.25 | 0 | 0 | 0 | 0 |

TABLE 3

| Compound to be tested | | Dosage [g/a] | Crop injury | | | Herbicidal effects | | | | |
|---|---|---|---|---|---|---|---|---|---|---|
| | | | Triticum aestivum | Hordeum vulgare | Avena sativa | Galium aparine | Veronica persica | Lamium purpureum | Papaver rhoeas | Matoricaria inodora |
| Compound of this invention | | 5.0 | 0 | 0 | 0 | 5 | 5 | 5 | 5 | 5* |
| | | 2.5 | 0 | 0 | 0 | 5 | 5 | 5 | 5 | 5 |
| | | 1.25 | 0 | 0 | 0 | 5 | 5 | 5 | 5 | 5 |
| Compound No. | 1 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 2 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 3 | 5.0 | 0 | 0 | 0 | 0 | 1 | 0 | 1 | 2 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 4 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 5 | 5.0 | 0 | 0 | 0 | 1 | 1 | 0 | 1 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 6 | 5.0 | 0 | 0 | 0 | 0 | 0 | 0 | 1 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 7 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 8 | 5.0 | 0 | 0 | 0 | 0 | 1 | 0 | 0 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 9 | 5.0 | 0 | 0 | 0 | 0 | 0 | 0 | 0 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 10 | 5.0 | 0 | 0 | 0 | 0 | 0 | 1 | 2 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 11 | 5.0 | 0 | 0 | 0 | 2 | 1 | 3 | 2 | 0 |
| | | 2.5 | 0 | 0 | 0 | 1 | 0 | 1 | 0 | 0 |
| | | 1.25 | 0 | 0 | 0 | 0 | 0 | 0 | 0 | 0 |
| | 12 | 5.0 | 0 | 0 | 0 | 2 | 2 | 3 | 2 | 3 |
| | | 2.5 | 0 | 0 | 0 | 2 | 2 | 1 | 1 | 2 |
| | | 1.25 | 0 | 0 | 0 | 0 | 1 | 1 | 0 | 0 |
| | 13 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 14 | 5.0 | 0 | 0 | 0 | 0 | 0 | 2 | 0 | 1 |
| | | 2.5 | 0 | 0 | 0 | 0 | 0 | 1 | 0 | 0 |
| | | 1.25 | 0 | 0 | 0 | 0 | 0 | 0 | 0 | 0 |
| | 15 | 5.0 | 0 | 0 | 0 | 0 | 0 | 2 | 1 | 1 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 16 | 5.0 | 0 | 0 | 0 | 2 | 3 | 2 | 2 | 3 |
| | | 2.5 | 0 | 0 | 0 | 1 | 3 | 2 | 1 | 2 |
| | | 1.25 | 0 | 0 | 0 | 0 | 2 | 0 | 0 | 0 |
| | 17 | 5.0 | 0 | 0 | 0 | 2 | 3 | 3 | 3 | |
| | | 2.5 | 0 | 0 | 0 | 1 | 3 | 2 | 1 | 2 |
| | | 1.25 | 0 | 0 | 0 | 0 | 2 | 0 | 0 | 0 |
| | 18 | 5.0 | 0 | 0 | 0 | 0 | 0 | 0 | 0 | 0 |
| | | 2.5 | 0 | 0 | 0 | 0 | 0 | 0 | 0 | 0 |
| | | 1.25 | 0 | 0 | 0 | 0 | 0 | 0 | 0 | 0 |
| | 19 | 5.0 | 0 | 0 | 0 | 0 | 0 | 2 | 1 | 2 |
| | | 2.5 | 0 | 0 | 0 | 0 | 0 | 0 | 0 | 1 |
| | | 1.25 | 0 | 0 | 0 | 0 | 0 | 0 | 0 | 0 |

TABLE 4-continued

| Compound to be tested | Dosage [g/a] | Damage* Triticum aestivum | Herbicidal effects Galium aparine | Veronica persica | Papaver rhoeas |
|---|---|---|---|---|---|
| Compound No. 21 | 5.0 | 0 | 0 | 0 | 1 |
|  | 2.5 | 0 | 0 | 0 | 0 |
|  | 1.25 | 0 | 0 | 0 | 0 |
| Compound No. 22 | 5.0 | 0 | 0 | 0 | 0 |
|  | 2.5 | 0 | 0 | 0 | 0 |
|  | 1.25 | 0 | 0 | 0 | 0 |
| Compound No. 23 | 5.0 | 0 | 0 | 0 | 0 |
|  | 2.5 | 0 | 0 | 0 | 0 |
|  | 1.25 | 0 | 0 | 0 | 0 |
| Compound No. 24 | 5.0 | 0 | 0 | 0 | 0 |
|  | 2.5 | 0 | 0 | 0 | 0 |
|  | 1.25 | 0 | 0 | 0 | 0 |
| Compound No. 25 | 5.0 | 0 | 0 | 0 | 1 |
|  | 2.5 | 0 | 0 | 0 | 0 |
|  | 1.25 | 0 | 0 | 0 | 0 |

*Damage: Crop damage from herbicide

As clearly seen from the Tables, the herbicidal composition of the present invention is harmless against wheats and has great herbicidal effects to weeds by soil and foliar cereal crops.

EXAMPLE 6

Optical active isomer of the compound represented by the formula (I) was prepared in accordance with the above formula (3).

Preparation of
(−)-2-(4-fluoro-3-trifluoromethylphenoxy)butanoic acid

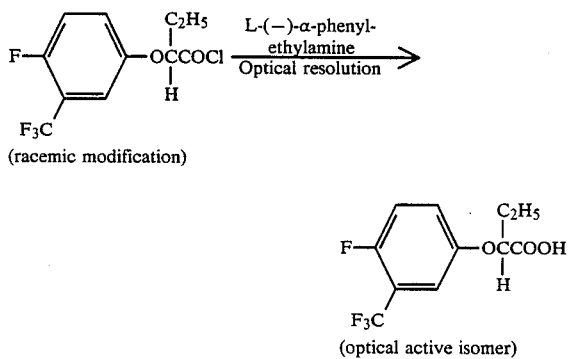

(racemic modification)

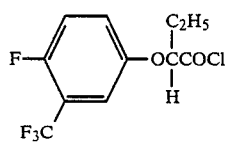

(optical active isomer)

After 10 g (37.6 mmole) of 2-(4-fluoro-3-trifluoromethylphenoxy)butanoic acid was dissolved in 50 ml of toluene, 4.55 g (37.6 mmole) of L-(−)-α-phenylethylamine was added to the solution and the mixture was stirred at 25° C. for 1 hour. Then, toluene was removed under reduced pressure to isolate the salt of L-(−)-α-phenylethylamine and 2-(4-fluoro-3-trifluoromethylphenoxy)butanoic acid. 14.5 g (37.5 mmole) of the resulting salt was added to 220 ml of carbon tetrachloride, and the mixture was dissolved by heating and stirring, gradually cooled to room temperature, and then allowed to stand at room temperature for 16 hours. After the precipitates were collected by filtration, recrystallization was repeated until the optical rotation of the precipitates become constant by the same manner as mentioned above. The resulting precipitates were suspended in a diluted hydrochloric acid and extracted with toluene. The separated toluene solution was dried over anhydrous sodium sulfate and toluene was removed under reduced pressure to obtain 1.5 g of the title compound. The compound had a specific rotatory activity $[\alpha]^{25°}$ $C_{\cdot D} = -51.4$ ° (C: 0.50 acetone), $[\alpha]^{23.3}{}_D = -53.8$ ° and $n^{26}{}_D = 1.4546$.

Preparation of
(-)-2-(4-fluoro-3-trifluoromethylphenoxy)butanoic acid chloride

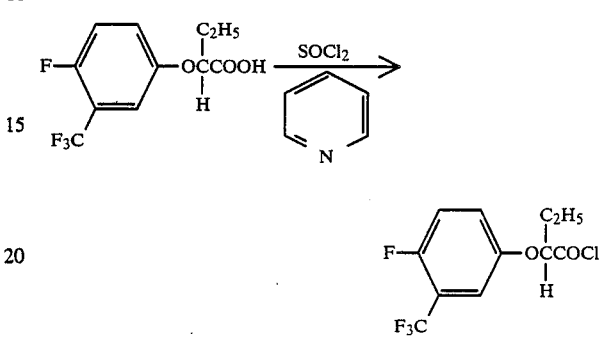

To 1.2 g (4.5 mmole) of (−)-2-(4-fluoro-3-trifluoromethylphenoxy)butanoic acid dissolved in 15 ml methylene chloride was added one drop of pyridine and further added dropwise 0.6 g of thionyl chloride. The reaction mixture was further stirred at room temperature for 4 hours and then thionyl chloride and methylene chloride were removed under reduced pressure to obtain 1.2 g of (−)-2-(4-fluoro3-trifluoromethylphenoxy)butanoic acid chloride. The resulting mixture was applied for the next reaction without purification.

Preparation of
(-)-N-benzyl-2-(4-fluoro-3-trifluoromethylphenoxy)-butanoic amide

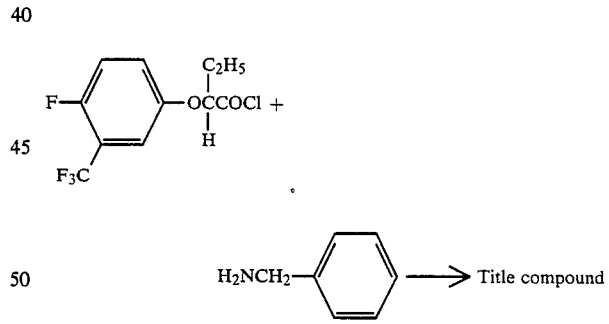

To 1.2 g (11.2 mmole) of benzylamine dissolved in 12 ml of methylene chloride was added dropwise 1.2 g of the above acid chloride dissolved in 8 ml of methylene chloride. The mixture was stirred at room temperature for 2 hours, washed with an aqueous acid solution and an aqueous alkali solution and then washed with water, and the methylene chloride solution was dried over anhydrous sodium sulfate. Methylene chloride was removed under reduced pressure and the residue was washed with hexane to give 0.45 g of the title compound (Yield: 37 %). The compound had a melting point of 81 to 82 ° C. and a specific rotatory activity $[\alpha]^{25°}$ $C_{\cdot D} = -41$ ° (C: 0.48 acetone), $[\alpha]^{23.3}{}_D = -39.2$ ° (C: 0.5 acetone) and melting point of 82 to 83 ° C.

EXPERIMENT 3

Comparative test of herbicidal effects between racemic modification and optical active isomer According to obstruction to accumulation of chlorophyll, the herbicidal activity was assessed. First of all, each 10 kinds of solutions having different concentration as shown in Table 5 of the compound obtained in Example 1 (racemic modification) and the compound obtained in Example 6 (optical active isomer) were prepared. Next, onto the petri dish having a diameter of 10 cm and putting down a filter paper therein, 10 ml of aforesaid each aqueous solution was added and 20 seeds of large crub-grass (*Digitalia sanguinalis*) were sowed in each of the petri dishes.

The seeds were grown up in a thermostat controlled at 25° C. under 5000 luxes illumination. One week after the sowing, 10 sheets of first leaf of large crub-grass were collected per each culture dish and extracted with 10 ml of hot ethanol. Then, absorbances of the extract at 663 nm and 645 nm were measured and total amounts of chlorophyll were calculated in accordance with the Arnon's calculation formula: total amount of chlorophyll (g/l) = 0.0202 $D_{645}$ + 0.00802 $D_{663}$ [see Plant Physiol., Vol. 24, 1, (1949)]. Evaluations concerning obstruction to accumulation of the chlorophyll were indicated as the value (%) relative to the total amount of chlorophyll extracted from the 10 sheets of first leaf of non-treated large crubgrass.

The results are shown in Table 5.

TABLE 5

| Concentration of the compound (ppm) | 1.1 | 1.0 | 0.9 | 0.8 | 0.7 | 0.6 | 0.5 | 0.4 | 0.3 | 0.2 |
|---|---|---|---|---|---|---|---|---|---|---|
| chlorophyll amount of racemic* | 8 | 9 | 10 | 12 | 15 | 17 | 25 | 29 | 42 | 62 |
| chlorophyll amount of optical** | 0 | 0 | 1 | 1 | 5 | 8 | 10 | 15 | 22 | 35 |

*Amount of chlorophyll at the division to which the racemic modification is added (% by weight).
**Amount of chlorophyll at the division to which the optical active isomer is added (% by weight).

As clearly seen from Table 5, the point at which accumulation of chlorophyll was obstructed to 90 % was 0.9 ppm when the racemic modification had been employed while it was 0.5 ppm when the optical active isomer had been employed. As the results, it can be found that the optical active isomer has higher herbicidal activities.

EXPERIMENT 4 (Foliar treatment)

Tests for confirmation of sinergistic effect of N-benzyl2-(4-fluoro-3-trifluoromethylphenoxy)-butanoic amide and other herbicidal compound A pot having an area of 1/5000 are was packed with upland soil (sandy loam soil) and then seeds of the following plants were sowed therein.

| Wheat | (Kobushi Komugi) |
|---|---|
| Blackgrass | *Alopecurus myosuroides* |
| Meadow grass | *Poa onnua* |

After covering seeds with soil, grown up was carried out in a glasshouse. When each plants were grown to 3 to 4-leaf stage, the compound of the present invention and the compound as shown in Table 6 were sprayed to the foliar with the amount as shown in Table 6. Thereafter, grown up of the plants was continued in the glasshouse and 30 days after the treatment, the crop injury and herbicidal effects (measured value and expected value) were assessed in accordance with the following formula:

$$\text{Measured value (\%)} = \left(1 - \frac{\text{Fresh weight of weed of treated division}}{\text{Fresh weight of weed of non-treated division}}\right) \times 100$$

Expected value (%) = $X + Y - (X \times Y)100$ wherein X is a depression percentage when treated with a herbicidal composition A with an amount of a g/are; and Y is a depression percentage when treated with a herbicidal composition B with an amount of b g/are.

(see H. R. Colby, Calculation of synergistic and competition reaction of the combination of herbicidal compositions, "Weeds", Vol. 15, pp. 20 to 22, (1967))

$$\text{Crop injury} = \left(1 - \frac{\text{Fresh weight of crop shoot of treated division}}{\text{Fresh weight of crop shoot of non-treated division}}\right) \times 100$$

The results are shown in Table 6.

TABLE 6

| Sprayed amount of the compound of this invention (g/ha) | Sprayed amount of the other compound (g/ha) | Damage against wheat (%) | Herbicidal effect (%) | | | |
|---|---|---|---|---|---|---|
| | | | *Alopecurus myosuroides* | | *Poa onnua* | |
| | | | Expected value | Observed value | Expected value | Observed value |
| 300 | — | 0 | — | 0 | — | 10 |
| — | Compound A-1 600 | 0 | — | 0 | — | 10 |
| — | Compound A-1 1000 | 0 | — | 8 | — | 20 |
| — | Compound A-1 1400 | 0 | — | 10 | — | 60 |
| 300 | Compound A-1 600 | 0 | 0 | 20 | 19 | 80 |
| 300 | Compound A-1 1000 | 0 | 8 | 35 | 38 | 90 |
| 300 | Compound A-1 1400 | 0 | 10 | 70 | 64 | 95 |
| — | Compound A-2 | 0 | — | 0 | — | 20 |

TABLE 6-continued

| Sprayed amount of the compound of this invention (g/ha) | Sprayed amount of the other compound (g/ha) | Damage against wheat (%) | Herbicidal effect (%) | | | |
|---|---|---|---|---|---|---|
| | | | Alopecurus myosuroides | | Poa onnua | |
| | | | Expected value | Observed value | Expected value | Observed value |
| — | Compound A-2 600 | 0 | — | 10 | — | 30 |
| — | Compound A-2 1000 | 0 | — | 20 | — | 70 |
| 300 | Compound A-2 1400 | 0 | 0 | 20 | 28 | 90 |
| 300 | Compound A-2 600 | 0 | 10 | 40 | 37 | 100 |
| 300 | Compound A-2 1000 | 0 | 20 | 80 | 73 | 100 |
| — | Compound A-3 1400 | 0 | — | 0 | — | 10 |
| — | Compound A-3 300 | 0 | — | 5 | — | 20 |
| — | Compound A-3 500 | 0 | — | 5 | — | 20 |
| 300 | Compound A-3 700 | 0 | 0 | 0 | 19 | 90 |
| 300 | Compound A-3 300 | 0 | 5 | 20 | 28 | 100 |
| 300 | Compound A-3 500 | 0 | 5 | 30 | 28 | 100 |
| — | Compound B 700 | 0 | — | 10 | — | 70 |
| — | Compound B 100 | 0 | — | 20 | — | 80 |
| — | Compound B 200 | 0 | — | 30 | — | 80 |
| 300 | Compound B 300 | 0 | 10 | 40 | 73 | 100 |
| 300 | Compound B 100 | 0 | 20 | 80 | 82 | 100 |
| 300 | Compound B 200 | 0 | 40 | 90 | 82 | 100 |

Experiment 5 (Soil treatment)

Tests for confirmation of sinergistic effect of N-benzyl2-(4-fluoro-3-trifluoromethylphenoxy)-butanoic amide and other herbicidal compound A pot having an area of 1/5000 are was packed with upland soil (sandy loam soil) and then seeds of the following plants were sowed therein.

| Wheat | (Kobushi Komugi) |
|---|---|
| Blackgrass | Alopecurus myosuroides |
| Meadow grass | Poa onnua |

After covering seeds with soil, grown up was carried out. Then, the compound of the present invention and the compound as shown in Table 7 were sprayed to the soil with the amount as shown in Table 7. Thereafter, grown up of the plants was continued in the glasshouse and 30 days after the treatment, the crop injury and herbicidal effects (measured value and expected value) were assessed in the same manner as in Experiment 6. The results are shown in Table 7.

TABLE 7

| Sprayed amount of the compound of this invention (g/ha) | Sprayed amount of the other compound (g/ha) | Damage against wheat (%) | Herbicidal effect (%) | | | |
|---|---|---|---|---|---|---|
| | | | Alopecurus myosuroides | | Poa onnua | |
| | | | Expected value | Observed value | Expected value | Observed value |
| 300 | — | 0 | — | 0 | — | 100 |
| — | Compound C 400 | 0 | — | 25 | 100 | — |
| — | Compound C 800 | 0 | — | 30 | — | 100 |
| 300 | Compound C 300 | 0 | 25 | 60 | 100 | 100 |
| 300 | Compound C 700 | 0 | 30 | 85 | 100 | 100 |
| — | Compound D 500 | 0 | — | 10 | — | 30 |
| — | Compound D 1000 | 0 | — | 60 | — | 50 |
| — | Compound D 2000 | 0 | — | 90 | — | 100 |

TABLE 7-continued

| Sprayed amount of the compound of this invention (g/ha) | Sprayed amount of the other compound (g/ha) | Damage against wheat (%) | Herbicidal effect (%) | | | |
|---|---|---|---|---|---|---|
| | | | *Alopecurus myosuroides* | | *Poa onnua* | |
| | | | Expected value | Observed value | Expected value | Observed value |
| 300 | Compound D 500 | 0 | 10 | 85 | 100 | 100 |
| 300 | Compound D 1000 | 0 | 60 | 100 | 100 | 100 |
| 300 | Compound D 2000 | 0 | 90 | 100 | 100 | 100 |

Compound C: α,α,α-Trifluoro-2,6-dinitro-N,N-dipropyl-p-toluene
Compound D: S-(p-chlorobenzyl)-N,N-diethylthiocarbamate As seen from Tables 6 and 7, when the compound of the present invention is combinedly used with other compounds shown in Table 6, the synergistic herbicidal effect can clearly been observed.

As explained above, the herbicidal composition of the present invention containing N-benzyl-2-(4-fluoro-3trifluoromethylphenoxy)butanoic amide of the present invention as an active ingredient is completely safty to cereals such as barley, wheat and oats and shows extremely excellent herbicidal activity against, needless to say, weeds to grasses such as foxtail and annual poa which exert a harmful influence upon a wheat crop, and against various broad-leaved weeds as well such as cleavers, speedwell, white dead nettle, red poppy and matoricaria which are weeds particularly difficult to control by the conventional herbicidal compositions.

Further, when the compound of the present invention is combinedly used with other herbicidal composition, excellent synergistic herbicidal effect is exhibited against the aforesaid weeds so that the amount of the compound to be sprayed can be diminished and reduction in producing cost of the crops can be accomplished.

We claim:

1. N-benzyl-2-(4-fluoro-3-trifluoromethylphenoxy)-butanoic amide represented by the formula:

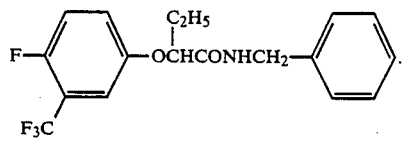

2. N-benzyl-2-(4-fluoro-3-trifluoromethylphenoxy)-butanoic amide according to claim 1, wherein said compound is (—)-N-benzyl-2-(4-fluoro-3-trifluoromethylphenoxy)butanoic amide.

3. A herbicidal composition comprising an herbicidally effective amount of N-benzyl-2-(4-fluoro-3-trifluoromethylphenoxy)butanoic amide represented by the formula:

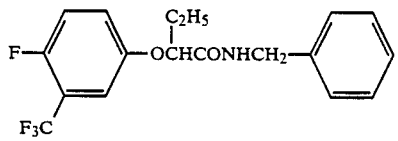

in an agricultural carrier.

4. The herbicidal composition according to claim 3, wherein said N-benzyl-2-(4-fluoro-3-trifluoromethylphenoxy)butanoic amide is (—)N-benzyl-2-(4-fluoro-3-trifluoromethylphenoxy)butanoic amide.

5. The herbidical composition of claim 3, containing 1 to 90% by weight of said amide.

6. The herbicidal composition of claim 4, containing 1 to 90% by weight of said amide.

* * * * *